United States Patent [19]

Chan

[11] Patent Number: 5,262,437
[45] Date of Patent: Nov. 16, 1993

[54] HOMO-PROSTAGLANDIN DERIVATIVES AS OCULAR HYPOTENSIVES

[75] Inventor: Ming Fai Chan, San Diego, Calif.

[73] Assignee: Allergan, Inc., Irvine, Calif.

[21] Appl. No.: 852,877

[22] Filed: Mar. 17, 1992

Related U.S. Application Data

[63] Continuation-in-part of Ser. No. 624,659, Dec. 10, 1990.

[51] Int. Cl.$^5$ .......................... A01N 37/08; C01C 3/02
[52] U.S. Cl. ..................... 514/530; 554/214; 560/122
[58] Field of Search ............ 560/122; 554/214; 514/530

[56] References Cited

U.S. PATENT DOCUMENTS

| | | | |
|---|---|---|---|
| 4,013,695 | 3/1977 | Lin | 554/214 |
| 4,024,167 | 5/1977 | Bundy et al. | 554/214 |
| 4,051,160 | 9/1977 | Bundy et al. | 554/214 |
| 4,105,682 | 8/1978 | Bundy | 554/214 |
| 4,122,100 | 10/1978 | Yankee | 554/214 |

FOREIGN PATENT DOCUMENTS

| | | |
|---|---|---|
| 0008227 | 2/1980 | European Pat. Off. |
| 0093380 | 9/1983 | European Pat. Off. |
| 0253094 | 1/1988 | European Pat. Off. |
| 2118686 | 11/1971 | Fed. Rep. of Germany |
| 7885M | 5/1970 | France |
| 8806448 | 9/1988 | PCT Int'l Appl. |

OTHER PUBLICATIONS

CA98 (7):49788a 1982.
CA95 (5):36216a 1981.
CA95 (1):1055v 1981.
CA 87(19):151771z 1977.
CA 98(25):215362d 1983.
CA 106(11):79289q 1986.
Cornette, James C. and Kirton, Kenneth, "Radioimmunoassay of Prostaglandins and their Metabolites", Mar. 4-5, 1976, 1977, *Proceedings of the International Symposium on Prostaglandins in Hematology*, Philadelphia, pp. 69-85, New York.
Tobias, L. D. et al., "The Biosynthesis of 1a,1b–DIHOMO–PGE$_2$* and 1a,1b–DIHOMO–PGF$_{20c}$ from 7, 10, 13, 16-Docosatetraenoic Acid by an Acetone-Pentane Powder of Sheep Vesicular Gland Microsomes", Sep. 1975, pp. 443-469, *Prostaglandins*, vol. 10, No. 3.

*Primary Examiner*—Paul J. Killos
*Attorney, Agent, or Firm*—Robert J. Baran; Martin A. Voet; James M. Hoch

[57] ABSTRACT

The invention relates to homo-prostaglandin derivatives. More particularly, the present invention concerns 1a-homo derivatives of naturally occurring and synthetic prostaglandins, the corresponding bis- and tri-shomo-prostaglandin compounds, and their 1-esters and salts. The homo-prostaglandin compounds of the present invention are potent ocular hypotensives, and are particularly suitable for the management of glaucoma.

16 Claims, No Drawings

HOMO-PROSTAGLANDIN DERIVATIVES AS OCULAR HYPOTENSIVES

This application is a continuation-in-part of pending application Ser. No. 07/624,659, filed on Dec. 10, 1990, and assigned to the same assignee as this application.

FIELD OF THE INVENTION

The present invention relates to homo-prostaglandin derivatives. More particularly, the present invention concerns 1a-homo derivatives of naturally occurring and synthetic prostaglandins, the corresponding bis- and trishomo-prostaglandin compounds, and their 1-esters and salts. The homo-prostaglandin compounds of the present invention are potent ocular hypotensives, and are particularly suitable for the management of glaucoma.

BACKGROUND OF THE INVENTION

The chemical structures of 1a-homo-prostaglandin $F_{2\alpha}$ (1a-homo-$PGF_{2\alpha}$) and the bishomo-$PGF_{2\alpha}$ compound are disclosed in Cornette, J. and Kirton, K. T., "Radioimmunoassay of Prostaglandins and their Metabolites" in Prostaglandins in Hematology, Spectrum Publications, Inc. 1977, pp. 69–85, in FIG. 7 (page 82). The paper describes a double-antibody radioimmunoassay system for measuring a primary prostaglandin and initial metabolites found in blood plasma as well as some of the primary urinary excretion products. The compounds listed in FIG. 7, including the bishomo-and homo-$PGF_{2\alpha}$ derivatives, were administered to rats subcutaneously in amounts equivalent to 1 mg $PGF_{2\alpha}$, and were used in the process of quantifying the urinary excretion of a prostaglandin metabolite in order to characterize the specificity of its antiserum. There is no disclosure of how the $PGF_{2\alpha}$ derivatives, including the homo- and bishomo-$PGF_{2\alpha}$ compounds, used for these studies were prepared, and the publication does not provide any data for the identification of these compounds. Nor is the composition of the subcutaneous injection preparations specified. The compounds were used for test purposes, unrelated to any pharmacological activity.

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical $\beta$-adrenoreceptor antagonists have traditionally been the drugs of choice for treating glaucoma.

Prostaglandins were earlier regarded as potent ocular hypertensives; however, evidence accumulated in the last decade shows that some prostaglandins are highly effective ocular hypotensive agents and are ideally suited for the long-term medical management of glaucoma (see, for example, Bito, L. Z. *Biological Protection with Prostaglandins* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins and their derivatives, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28(suppl), 284 (1987)].

The isopropyl ester of $PGF_{2\alpha}$ has been shown to have significantly greater hypotensive potency than the parent compound, which was attributed to its more effective penetration through the cornea. In 1987 this compound was described as "the most potent ocular hypotensive agent ever reported"[see, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed May 25, 1989). Similarly, 11,15- 9,15- and 9,11-diesters of prostaglandins, for example 11,15-dipivaloyl $PGF_{2\alpha}$ are known to have ocular hypotensive activity. See the co-pending patent applications U.S. Ser. No. 385,645 filed Jul. 27, 1990; 584,370 which is a continuation of U.S. Ser. No. 386,312, and U.S. Ser. No. 585,284 which is a continuation of U.S. Ser. No. 386,834, where the parent applications were filed on 27 Jul. 1989. The disclosures of these patent applications are hereby expressly incorporated by reference.

SUMMARY OF THE INVENTION

We have found that certain homo derivatives of $PF_{2\alpha}$ and other naturally occurring or synthetically prepared, homo-prostaglandins, are potent ocular hypotensive agents. We have further found that such compounds are significantly more potent than their respective parent compounds and, surprisingly, cause no or significantly lower ocular surface hyperemia than the parent compounds. The favorable separation between the hypotensive activity of these compounds and the undesired effect of ocular surface hyperemia is particularly apparent at lower doses.

The present invention relates to a method of treating ocular hypertension which comprises applying to the eye an amount sufficient to treat ocular hypertension of a compound of formula (I)

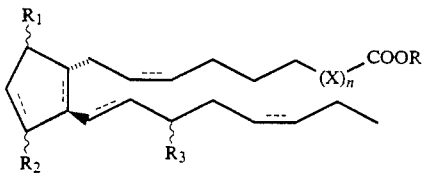

wherein the wavy line attachments indicate either alpha ($\alpha$) or beta ($\beta$) configuration; hatched lines indicate $\alpha$ configuration, solid triangles are used to indicate $\beta$ configuration; the dashed bonds represent a single bond or a double bond which can be in the cis or trans configuration; R is hydrogen or a pharmaceutically acceptable cation, or a saturated or unsaturated acyclic hydrocarbon group having from 1 to about 6 carbon atoms; X is a $-C(R_4,R_5)-$ group; n is 1, 2 or 3; one of $R_1$ and $R_2$ is $=O$, $-OH$ or a $-O(CO)R_6$ group, and the other one is $-OH$ or $-O(CO)R_6$, or $R_1$ is $=O$ and $R_2$ is H; $R_4$ and $R_5$ independently are hydrogen, or a saturated or unsaturated acyclic hydrocarbon group having from 1 to about 6 carbon atoms; $R_6$ is a saturated or unsaturated acyclic hydrocarbon group having from 1 to about 20 carbon atoms, or $-(CH_2)_mR_7$ wherein m is 0-10, and $R_7$ is an aliphatic ring from about 3 to about 7 carbon atoms, or an aromatic or heteroaromatic ring; or a pharmaceutically acceptable salt thereof.

In another aspect, the present invention relates to a pharmaceutical composition comprising a therapeutically effective amount of a compound of formula (I)

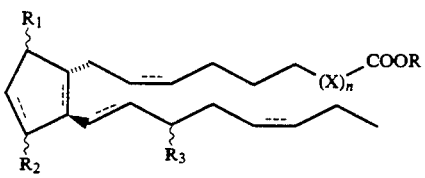

wherein $R_3$ is $-OH$ or a $-O(CO)R_6$ group, and the other symbols and substitutent are as defined above, in combination with a pharmaceutical carrier.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable salt thereof, in admixture with a non-toxic, ophthalmically acceptable liquid vehicle.

In a still further aspect, the present invention relates to homo-prostaglandin derivative of the formula (I), wherein the substituents and symbols are as defined hereinabove, or a pharmaceutically acceptable salt of such compounds.

In another aspect, the present invention relates to a pharmaceutical product, comprising:
- a container adapted to dispense its contents in a metered form; and
- an ophthalmic solution therein, as hereinabove defined.

DETAILED DESCRIPTION OF THE INVENTION

Prostaglandins can be described as derivatives of prostanoic acid which has the following structural formula:

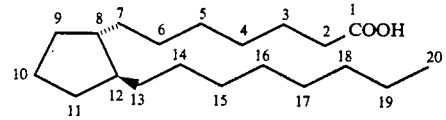

Various types of prostaglandins are known, depending on the structure and substituents carried on the alicyclic ring of the prostanoic acid skeleton. Further classification is based on the number of unsaturated bonds in the side chains indicated by numerical subscripts after the generic type of prostaglandin [e.g., prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\alpha}$)].

The present invention relates to the use of homo-prostaglandin compounds, and their derivatives and analogues as ocular hypotensives. The prostaglandin derivatives used in accordance with the present invention are encompassed by the following structural formula (I)

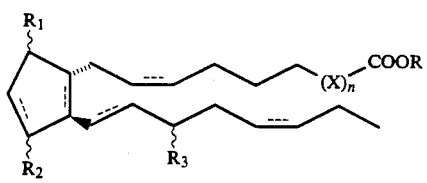

wherein the substituents and symbols are as hereinabove defined.

The above formula includes homo derivatives of prostaglandins of the F, D, E, A and B series. A preferred group of the compounds of the present invention is encompassed by the following formula (II)

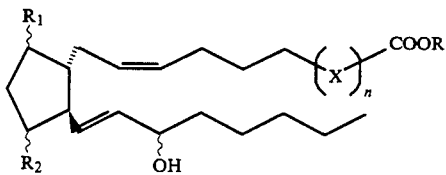

wherein $R_1/R_2$ is —OH/—OH, =O/—OH, —OH/=O and the esters of these compounds. This definition includes $PGF_2$, $PGE_2$ and $PGD_2$ derivatives.

Particularly preferred are the $PGF_{2\alpha}$ derivatives of the formula (III)

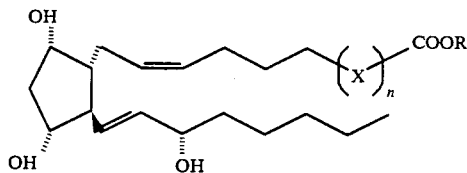

and their 9- and/or 11- and/or 15-esters.

In all of the above formulae, as well as in those provided hereinafter, the dotted lines on bonds between carbons 5 and 6 (C-5), between carbons 13 and 14 (C-13), between carbons 8 and 12 (C-8), between carbons 10 and 11 (C-10) and between carbons 17 and 18 (C-17) indicate a single or a double bond which can be in the cis or trans configuration. If two solid lines are used that indicates a specific configuration for that double bond. Hatched lines at positions C-9, C-11 and C-15 indicate the α configuration. If one were to draw the β configuration, a solid triangular line would be used.

The naturally occurring stereochemistry of $PGF_{2\alpha}$ includes the C-9, C-11, and C-15 hydroxyl groups in the α configuration. In the compounds used in accordance with the present invention, however, prostaglandins having the C-9 or C-11 or C-15 substituents in β configuration are also contemplated. As hereinabove mentioned, in all formulas provided herein broken line attachments to the cyclopentane ring indicate substituents in the α configuration. Thickened solid line attachments to the cyclopentane ring indicate substituents in the α configuration. For instance, 9β-PGF compounds have the same structure as $PGF_\alpha$ compounds, except that the hydroxyl at the C-9 position is in the β configuration. Also, the broken line attachment of the hydroxyl group or other substituent to the C-11 and C-15 carbon atoms signifies the β configuration; therefore, compounds with the epi configuration for the hydroxyl group at C-15 are designated by using 15β and if there is no indication of the β configuration, the configuration is assumed α.

In the above formula the term "saturated or unsaturated acyclic hydrocarbon group" is used to refer to straight or branched, chained, saturated or unsaturated hydrocarbon groups having from one to about 6, preferably one to about 4 carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

The definition of $R_6$ may include a cyclic component, —$(CH_2)_nR_7$, wherein n is 0–10, $R_7$ is an aliphatic ring from about 3 to about 7 carbon atoms, or an aromatic or heteroaromatic ring. The "aliphatic ring" may be saturated or unsaturated, and preferably is a saturated ring having 3–7 carbon atoms, inclusive. As an aromatic ring, $R_7$ preferably is phenyl, and the heteroaromatic rings have oxygen, nitrogen or sulfur as a heteroatom. Preferably n is 0–4.

Preferred are those $PGF_{2\alpha}$ derivatives in which n is 1 or 2.

Particularly preferred are the $PGF_{2\alpha}$ derivatives in which $R_4$ and $R_5$ are both hydrogen.

Preferred representatives of the compounds within the scope of the present invention are 1a-homo prostaglandin $F_{2\alpha}$ and the 9- and/or 11- and/or 15-esters of this compound.

A typical synthesis route for the preparation of the compounds of this invention is illustrated in Reaction Scheme 1. The reaction partners and reaction conditions for the sequential reaction steps are as follows:

a) 3,4-dihydro-4H-pyran, pyridinium p-toluenesulfonate (catalyst), $CH_2Cl_2$, 25° C.;

b) diisobutylaluminium hydride, $CH_2Cl_2$, −78° C., 2 hrs;

c) KN$(SiMe_3)_2$ (6 equivalents), $Ph_3P^+(CH_2)_5CO_2H$ Br⁻ (3 equivalents), THF, −78° to 25° C.;

d) $CH_2N_2$, $Et_2O$;

e) MeOH, pyridinium p-toluenesulfonate (catalyst), 5° C.;

f) LiOH; THF/$H_2O$, 25° C.

A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system, a substantially neutral pH being preferred. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 μl.

The invention is further illustrated by the following non-limiting Examples.

EXAMPLE 1

Synthesis of a 1a-Homo Prostaglandin $F_{2\alpha}$ ($-$)-6$\beta$-(3S-hydroxyoct-1-enyl)-7$\alpha$-hydroxy-2-oxabicyclo[3.3.0]octan-3-one (obtained from Chinion Chemical Company, Hungary; 1.48 g, 5.5 mmol) and 4H-2,3-dihydropyran (1.5 ml, 16.5 mmol) were dissolved in methylene chloride (6 ml) and pyridinium p-toluenesulfonate (PPTS, 70 mg, 0.28 mmol) was added. The solution was stirred at 25° C. for 16 h. The solvent and volatiles were evaporated under reduced pressure to give a thick oil. Flash chromatography (silica gel, 20-30% ethyl acetate in hexane) yielded 2.18 g (91%) of the pure di-THP ether, $R_f$ 0.10 (25% ethyl acetate in hexane).

The di-THP ether obtained above (196 mg, 0.45 mmol) was dissolved in methylene chloride (1.5 ml) and cooled to $-78°$ C. in a dry ice-acetone bath. A solution of diisobutylaluminum hydride in methylene chloride (1.0M, 0.90 ml, 0.90 mmol) was added dropwise. After stirring for 2 h at $-78°$ C., methanol (0.5 ml) was added dropwise. The reaction mixture was poured into 10% citric acid and extracted with ethyl acetate. The combined extracts were washed with saturated sodium bicarbonate and brine, dried over magnesium sulfate and concentrated to give 194 mg of di-THP lactol as colorless oil.

Ethoxycarbonylpentyltriphenylphosphonium bromide (611 mg, 1.34 mmol) and potassium hexamethyldisilazide (533 mg, 2.67 mmol) were placed in a flame-dried 10 ml round bottom flask flushed with argon and cooled to $-78°$ C. Tetrahydrofuran (THF, 5 ml) was introduced into the flask and the reaction was allowed to warm up to 25° C. A red solution was formed and the flask was recooled to $-78°$ C. A solution of the di-THP lactol obtained above in THF (2 ml) was slowly added. The solution was allowed to warm up to room temperature overnight (16 h). The solvents were evaporated under vacuum and the residue was taken up in ethyl acetate, washed with water and brine and concentrated. The residue was dissolved in methanol and ethereal diazomethane was added until a yellow color persisted. A few drops of acetic acid were added and the solution was reconcentrated. The crude product was treated sequentially with PPTS in methanol at 50° C. (to remove the THP ethers) and 0.5M lithium hydroxide/THF (to saponify the ethyl ester) to give a 1a-homo $PGF_{2\alpha}$. Purification was achieved by preparative thin layer chromatography (silica gel plates, acetic acid/methanol/methylene chloride 1:10:89), $R_f$ 0.2-0.3, yield 53.2 mg.

$^1$H NMR (300 MHz, $CDCL_3$): $\delta$5.52(2H, ABX, $J_{AB}=15.3$, $J_{AX}=6.3$, $J_{BX}=8$ Hz), 5.39 (2H, complex AB), 4.18 (1H,t,J=4 Hz), 4.08 (1H, q,J=6.5 Hz), 3.95(1H,m), 1.9-2.4(13 Hm), 2.34 (3H,t,J=7.2 Hz), 1.2-1.8 (10H, m), 0.88 ppm (3H,t,J=6.5 Hz);

$^{13}$C NMR (75 MHz), $CDCl_3$): $\delta$178.35, 135.46, 133.21, 130.42, 128.66, 73.27, 72.60, 55.38, 49.89, 42.56, 36.84, 33.60, 31.55, 29.27, 28.64, 26.49, 25.25, 25.02, 24.05, 22.41, 13.80 ppm;

MS (EI, TMS derivative of methyl ester): m/z 598.6 (M+, 1.6%), 508 (12), 437, (18), 347 (10), 321 (11), 217 (13), 191 (39), 173 (18), 147 (19), 129 (13), 75 (17), 73 (100); HRMS (EI, TMS derivative of methyl ester): calculated for $C_{31}H_{62}O_5Si_3$: 598.3903, found: 598.3904.

EXAMPLE 2

Intraocular Pressure Reducing Activity

Experimental quantities of the test compounds were prepared in an ophthalmic formulation containing 0.1% polysorbate (Tween 80)-10 mM TRIS. One eye of each experimental animal was treated by applying one 25 μl drop of the drug formulation to the ocular surface, the contralateral eye received 25 μl of vehicle as a control. Intraocular pressure was measured by applanation pneumatonometry immediately before drug administration and at subsequent, predetermined times thereafter. New Zealand albino/dutch belted cross rabbits were employed as experimental animals.

Ocular surface hyperemia was assessed by observation at predetermined times after drug administration and is described as either present or absent.

The results are shown in the following Table:

TABLE I

| PROSTANOID | (DOSE %) | 0 | 1.0 | 2.0 | 3.0 | 4.0 | 6.0 |
|---|---|---|---|---|---|---|---|
| | | | EFFECT ON INTRAOCULAR PRESSURE (mmHg) AT PREDETERMINED TIMES POST-ADMINISTRATION | | | | | |
| homo-PGF$_{2\alpha}$ | 0.01% | — | −6.1** | −6.2** | −5.3** | −0.1 | −0.4 |
| homo-PGF$_{2\alpha}$ | 0.1% | — | −2.9 | −4.1** | −4.1** | −3.5** | −0.25 |
| homo-PGF$_{2\alpha}$ | 1.0% | — | +0.2 | −2.1 | −4.1 | −8.3** | −6.7** |
| | | | % ANIMALS EXHIBITING OCULAR SURFACE HYPEREMIA | | | | | |
| homo-PGF$_{2\alpha}$ | 0.01% | — | 0 | 0 | 0 | 0 | 0 |
| homo-PGF$_{2\alpha}$ | 0.1% | — | 100 | 87.5 | 87.5 | 67.5 | 12.5 |
| homo-PGF$_{2\alpha}$ | 1.0% | — | 100 | 100 | 100 | 100 | 100 |

\* p < 0.05
\*\*p < 0.01
n = 8

The foregoing description details specific methods and compositions that can be employed to practice the present invention, and represents the best mode contemplated. However, it is apparent from one of ordinary skill in the art that further compounds with the desired pharmacological properties can be prepared in an analogous manner, and that the disclosed compounds can be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

We claim:

1. A method of treating ocular hypertension which comprises applying to the eye an amount sufficient to treat ocular hypertension of a compound of formula (I)

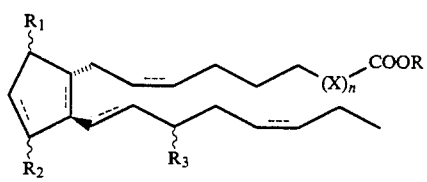

wherein the wavy line attachments indicate either alpha (α) or beta (β) configuration; hatched lines indicate α configuration, solid triangles are used to indicate β configuration; the dashed bonds represent a single bond or a double bond which can be in the cis or trans configuration; R is hydrogen or a pharmaceutically acceptable cation, or a saturated or unsaturated acyclic hydrocarbon group having from 1 to about 6 carbon atoms; X is a —C(R$_4$,R$_5$)— group; n is 1, 2 or 3; one of R$_1$ and R$_2$ is =O, —OH or a —O(CO)R$_6$ group, and the other one is —OH or —O(CO)R$_6$, or R$_1$ is =O and R$_2$ is H; R$_3$ is —OH or a —O(CO)R$_6$ group; R$_4$ and R$_5$ independently are hydrogen, or a saturated or unsaturated acyclic hydrocarbon group having from 1 to about 6 carbon atoms; R$_6$ is a saturated or unsaturated acyclic hydrocarbon group having from 1 to about 20 carbon atoms, or —(CH$_2$)$_m$R$_7$ wherein m is 0–10, and R$_7$ is an aliphatic ring from about 3 to about 7 carbon atoms, or an aromatic or heteroaromatic ring; or a pharmaceutically acceptable salt thereof.

2. The method of claim 1 wherein said compound of formula (I) is selected from the group consisting of naturally occurring prostaglandins of the D, E and F series.

3. The method of claim 1 wherein said compound is a prostaglandin derivative of the formula (II)

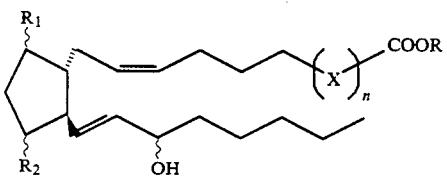

wherein R$_1$/R$_2$ is —OH/—OH, =O/—OH, —OH/=O, and the other symbols and substituents are as defined in claim 1, or a —O(CO)R$_6$ ester thereof.

4. The method of claim 3 wherein said compound is a PGF$_{2\alpha}$ derivative of the formula (III)

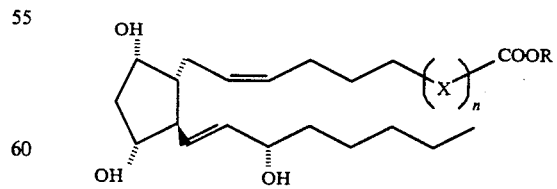

wherein the symbols and substituents are as defined in claim 1.

5. The method of claim 4 wherein in the formula n is 1 or 2, and R and X are as defined in claim 1.

6. The method of claim 5 wherein in the formula R$_4$ and R$_5$ are both hydrogen.

7. The method of claim 6 wherein said compound is 1a-homo prostaglandin $F_{2\alpha}$.

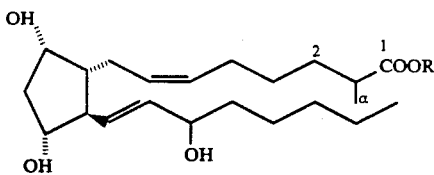

8. An ophthalmic solution comprising a therapeutically effective amount of a compound of formula (I)

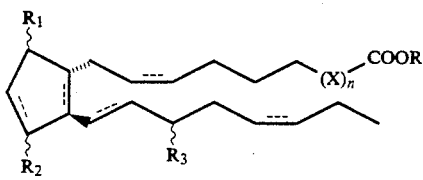

wherein the wavy line attachments indicate either alpha ($\alpha$) or beta ($\beta$) configuration; hatched lines indicate $\alpha$ configuration, solid triangles are used to indicate $\beta$ configuration; the dashed bonds represent a single bond or a double bond which can be in the cis or trans configuration; R is hydrogen or a pharmaceutically acceptable cation, or a saturated or unsaturated acyclic hydrocarbon group having from 1 to about 6 carbon atoms; X is a —C($R_4$,$R_5$)— group n is 1, 2 or 3; one of $R^1$ and $R_2$ is =O, —OH or a —O(CO)$R_6$ group, and the other one is —OH or —O(CO)$R_6$, or $R_1$ is =O and $R_2$ is H; $R_3$ is —OH or a —O(CO)$R_6$ group; $R_4$ and $R_5$ independently are hydrogen, or a saturated or unsaturated acyclic hydrocarbon group having from 1 to about 6 carbon atoms; $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ring from about 3 to about 7 carbon atoms, or an aromatic or heteroaromatic ring; or a pharmaceutically acceptable salt thereof, in admixture with a non-toxic ophthalmically acceptable liquid vehicle.

9. The ophthalmic solution of claim 8 comprising at least one ingredient selected from the group of an ophthalmically acceptable preservative, buffer system, antioxidant and chelating agent.

10. The ophthalmic solution of claim 9 wherein said compound of formula (I) is selected from the group consisting of naturally occurring prostaglandins of the D, E and F series.

11. The ophthalmic solution of claim 10 wherein said compound is a prostaglandin derivative of the formula (II)

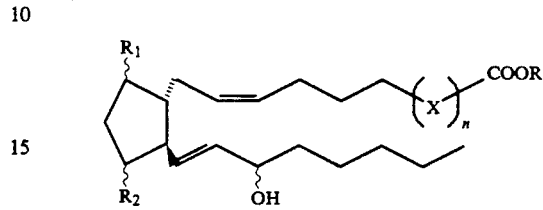

wherein $R_1$/$R_2$ is —OH/—OH, =O/—OH, —OH/=O, and the other symbols and substituents are as defined in claim 8, or a —O(CO)$R_6$ ester thereof.

12. The ophthalmic solution of claim 11 wherein said compound is a $PGF_{2\alpha}$ derivative of the formula (III)

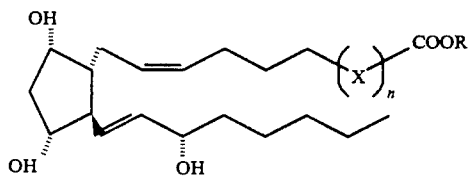

wherein the symbols and substituents are as defined in claim 8.

13. The ophthalmic solution of claim 12 wherein in the formula n is 1 or 2, and R and X are as defined in claim 8.

14. The ophthalmic solution of claim 13 wherein in the formula n is 1 or 2, and R and X are as defined in claim 8.

15. The ophthalmic solution of claim 14 wherein in the formula $R_4$ and $R_5$ are both hydrogen.

16. A pharmaceutical product, comprising
a container adapted to dispense its contents in metered form; and
an ophthalmic solution therein, as defined in claim 8.

* * * * *